United States Patent [19]
Iwantscheff et al.

[11] 4,094,640
[45] June 13, 1978

[54] METHOD FOR PROCESSING BIOMATERIALS

[75] Inventors: Georg Iwantscheff, Nuremberg; Egmont Scheubeck, Erlangen, both of Germany

[73] Assignee: Siemens Aktiengesellschaft, Munich, Germany

[21] Appl. No.: 764,541

[22] Filed: Jan. 31, 1977

[30] Foreign Application Priority Data

Feb. 12, 1976 Germany .............................. 2605560

[51] Int. Cl.² ........................................... G01N 31/12
[52] U.S. Cl. ........................... 23/230 PC; 23/253 PC
[58] Field of Search ............. 23/230 PC, 253 PC; 73/190 R, 191

[56] References Cited
U.S. PATENT DOCUMENTS

| | | | |
|---|---|---|---|
| 1,247,998 | 11/1917 | Parr | 73/191 |
| 3,485,565 | 12/1969 | Kaartinen | 23/253 PC X |
| 3,542,121 | 11/1970 | Kaartinen | 23/253 PC UX |
| 3,665,761 | 5/1972 | Gregory | 73/190 R |
| 3,844,716 | 10/1974 | Woakes | 23/253 PC |

OTHER PUBLICATIONS

C.E. Gleit et al, Anal. Chem., vol. 34, No. 11, pp. 1454-1457, Oct. 1962.
B. Morsches et al, J. Anal. Chem., vol. 219, pp. 61-68, 1966.

*Primary Examiner*—Joseph Scovronek
*Attorney, Agent, or Firm*—Kenyon & Kenyon, Reilly, Carr & Chapin

[57] ABSTRACT

A method for processing biomaterial, particularly meat, in which coarsely comminuted biomaterial with a moisture of up to 80% is dried in a processing vessel down to a residual moisture of about 5–10% and subsequently burned at a pressure of 20 to 40 bar in pure oxygen permitting metal traces, particularly mercury, cadmium, lead and arsenic, to be readily determined analytically in the process solution.

12 Claims, 1 Drawing Figure

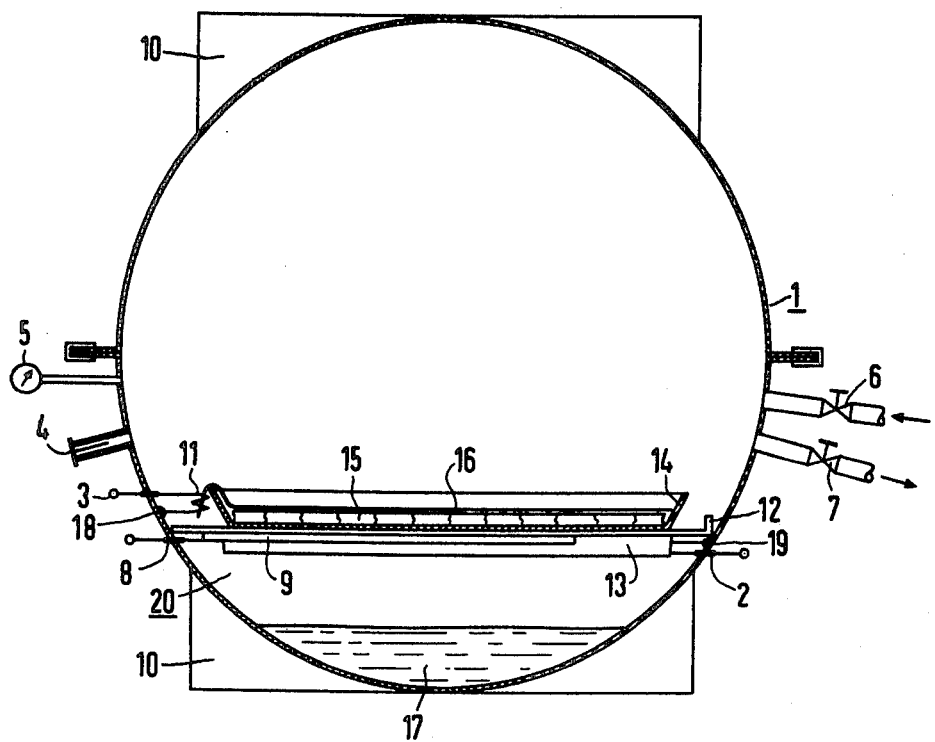

METHOD FOR PROCESSING BIOMATERIALS

BACKGROUND OF THE INVENTION

This invention relates to the processing of biomaterials in general and more particularly to an improved method for finding metal traces in a biomaterial.

The importance of determining metal traces in organic materials, particularly foodstuffs, is increasing. As a rapid method for multielement analysis, the X-ray fluorescence analysis (RFA) is available. Without preceding enrichment of the metal traces, however, the sensitivity of this analytical method does not, in all cases, meet the more recent requirements of foodstuff control. In addition, the sample to be examined must be present in a form suitable for X-ray fluorescence analysis. For these reasons, a rapid method for the enrichment of metal traces and a sample presentation suitable for the analysis are prerequisites for the economical use of the X-ray fluorescence analysis in examining a large number of food samples.

The known chemical analysis and preparation techniques require a large amount of time for processing, e.g., breaking down, the necessary amounts of sample and are not reliable enough for the quantitative enrichment of metal traces. Thus, wet processing methods with oxidizing agents, for instance, require several hours for breaking down 20 g of meat and the sample solutions obtained are loaded with a large amount of foreign salts and their admixtures.

It is also known to process or break down biological materials with activated oxygen by the microwave process, cf. C. E. Gleit and W. D. Holland, Anal. Chem 34, (1962), p. 1454, in pure flowing oxygen, see also, for instance, B. Morsches, G. Toelg; Z. anal. Chem. 219 (1966), p. 61, or in pure oxygen at elevated pressure, see, for instance M. Berthelot, Ann. Chim. Phys. 26 (1892), p. 555. Heretofore, only quantities of up to about 1 g have been used. The quantitative processing (breakdown) of meat in pure oxygen at elevated pressure requires suitable communition and drying. The drying methods used so far in open systems involve the danger of metal losses due to volatilization. In drying in a closed system, the evaporated water must be separated from the sample, for instance, by condensation. Insufficient comminution of the sample and excessively high residual moisture of the sample cause incomplete processing, while a finely distributed, very dry material can lead to an explosion. For enriching metal traces, methods are known from the literature (see, for instance, R. Pueschel, Talanta 16, (1969), p. 351) which detect quantitites down to a few micrograms. All these methods are not directly applicable to the determination of metal traces in food either in the required short analysis time or with the desired sensitivity. Without appropriate preparation of the samples, traces of metallic poisons cannot be determined in biomaterials, for instance, with RFA, in the order of magnitude prescribed by laws (Hg: 0.000002%; Cd: 0.000008%, Pb: 0.00002% and As: 0.000005%).

SUMMARY OF THE INVENTION

It is therefore an object of the present invention to provide an improved method for processing (breaking down) biomaterials, by means of which it is possible to process organic substances, particularly meat, in a quantity of about 20 g in less than 30 minutes in a simple manner, while at the same time enriching the matrix and without using foreign acids or alkalis. It should be possible to obtain from the resulting solution precipitates suitable for the X-ray fluorescence analysis.

To solve this problem, a moist sample of the biomaterial, particularly meat, is pre-dried in a closed pressure vessel and subsequently burned in oxygen. In this process, no ash is produced which needs to be digested, but only gaseous and liquid products, the latter consisting of the condensate of the drying and combustion processes. In this condensate, all the traces to be determined are quantitatively present, quasi-dissolved in its own juice.

According to one preferred embodiment of the invention, the drying is continued to a residual moisture of 5 to 10%. Particularly good data could be obtained if 20 to 30 g of the biomaterial with a water content of 70 to 90% were used. In the case of meat, in particular, the pre-drying usually takes place at 20 mbar and 110° C. The combustion is particularly favorable at an oxygen pressure of 30 to 40 bar.

According to the method of the present invention, a 20 g sample of the biomaterial with a water content of 80% can be pre-dried in a closed pressure vessel at a pressure of about 20 mbar to a residual moisture of 5 to 10% in less than 30 minutes and subsequently be burned in oxygen at 30 to 40 bar.

For carrying out the method according to the invention, a spherical processing vessel such as a Berthelot calorimetric bomb with external cooling has been found particulary well suited. The water vapor produced in the drying of the biomaterial is preferably condensed to a large extent at the wall of the closed pressure vessel, which is cooled to about 10° C. The combustion is preferably accomplished by an ignition device. The metal traces can be determined from the process solution without the addition of chemicals. They can also be precipitated out by a complex former in a special precipitation and filtering apparatus. The precipitate can be presented by filtration on a diaphragm filter in a form suitable for the analysis.

With the method according to the present invention, biomaterials, in particular meat, can be processed in a short time, in less than 30 minutes, without other additions. After suitable enrichment, trace metals can be determined from the solution obtained, in which the unknown metals are present, by means of X-ray fluorescence analysis. The numerical results of blank tests obtained here are understandably very low.

A closed vessel suitable for implementing the method according to the present invention is preferably vertically disposed. The processing vessel may consist of chromium-nickel-molybdenum steel and has a cooling device for its outer surface. The sample is dried in the processing vessel, for instance, by high frequency induction heating, but mainly by resistance heating. The shape of the heater is matched to the shape of the base area of the sample container. The ignition for burning the sample material is provided either by an incandescent wire of platinum or by means of a high voltage spark.

To carry out the method according to the invention, a sample of 20 to 30 g of the biomaterial to be examined, with about 80% moisture, can be comminuted, if desired, for homogenizing. The comminuted sample is placed into a processing vessel equipped with a removable lid and external cooling in a sample container of quartz and, while being heated, is dried in the closed vessel. The wall can be cooled during the drying. Then, pure oxygen is admitted and caused to fill the vessel up to 40 bar pressure and subsequently, the combustion takes place. After cooling down, the trace elements, poisons and the like can be determined analytically from the removed process solution.

With the method according to the present invention, traces of metallic poisons such as, in particular, mercury, cadmium, lead and arsenic, in biomaterials can be determined if they are present in the order of magnitude from $10^{-4}$ to $10^{-6}\%$. It is also suited for determining other elements by known analytical methods such as atomic absorption spectrophotometry, colorimetry or polarography.

BRIEF DESCRIPTION OF THE DRAWING

The drawing is a schematic longitudinal cross section of a processing vessel according to the present invention for biomaterial, particularly meat.

DETAILED DESCRIPTION OF THE INVENTION

The processing vessel 20 is equipped with a fast closing lid 1. In the lower part are disposed two pressure proof, electrically insulated feedthroughs 2 and 3, one for a drying device 13, and one for an ignition device 11, a safety valve 4, a manometer 5, two gas feedthroughs 6 and 7 with reducing valves for the oxygen supply and discharge and an electrically insulated feedthrough 8 for a thermocouple 9. The processing vessel is cooled by means of a cooling coil or a cooling jacket 10. An ignition wire 11 is also disposed in the vessel. A sample container 14 of quartz rests on a heater 13 by means of a mounting 12. The biomaterial 15 is covered with a filter paper 16. The solution, which collects at the bottom of the processing vessel after the method according to the present invention is carried out, is designated 17. Two electrical grounding points 18 and 19 for the heater and the incandescent wire are also shown.

EXAMPLE 1

20 g of a comminuted meat sample are covered in the quartz sample container 14 with filter paper 16 and placed in the holder 12 of the pressure processing apparatus. The apparatus is closed and evacuated to about 20 mbar through the gas feed-through 7, and the sample is dried by means of the heating plate 13 at 110° C. Subsequently, the vessel is filled with oxygen to a pressure of 35 to 40 bar and the ignition wire 11 is actuated. After a brief pressure rise, a pressure of 40 to 50 bar adjusts itself again after a few minutes. Then the overpressure is relieved via the gas discharge valve and the apparatus is opened by removing the entire lid. The process solution 17 is drawn up by means of a hose pump or a piston dosing device or let out at the bottom via a valve. Thereupon after rinsing with some distilled water, the collected process solution is placed together with the rinsing liquid in a 50 ml measuring flask and the latter is filled up with water to the 50 ml. For routine analyses, the time required for the processing of a sample is about 10 to 15 minutes if two processing equipments are used alternatingly. The trace elements cadmium, mercury, arsenic and lead can easily be detected from the process solution.

EXAMPLE 2

30 g of coarsely comminuted fresh carrots are covered in the sample container 14 with filter paper 16 and placed in the processing apparatus. The apparatus is closed and evacuated to about 20 mbar. Subsequently, the carrot sample is dried for about 10 minutes. Because the maximum current for the resistance heater 13 is limited, the temperature at the sample container cannot exceed 110° C. The wall of the processing equipment is cooled to about 10° C during the entire processing operation. After the drying, the organic matrix is burned in oxygen at a pressure of about 40 bar. The water vapor from the drying of the biomaterial and the combustion products of the organic portion form, in the bottom part of the processing apparatus, a weakly acid solution, in which metal traces are enriched. They can be determined therefrom by suitable analytic methods.

EXAMPLE 3

To 5 g of animal or vegetable fat i.e. a biomaterial which is essentially water-free (containing no more than 1-2% water), in the sample container 14 about 1 ml of distilled water is added and the sample is covered with filter paper 16. 9 ml of distilled water are placed in the bottom part of the processing apparatus and the latter is closed. After the external cooling is started, the apparatus is evacuated to about 20 mbar and pre-drying is effected for a few minutes with the resistance heater 13 by evaporating the water in the sample container. The heater is then switched off and the biomaterial is burned in oxygen at about 40 bar. After the processing, the metal traces can be determined analytically in the solution in the bottom part of the processing equipment as in Examples 1 and 2.

We claim:

1. A processing method for breaking down biomaterial comprising:
   a. disposing 20–30g of a moist sample of the biomaterial in a closed pressure vessel;
   b. predrying said sample down to a residual moisture of 5–10%;
   c. cooling the wall of the pressure vessel to about 10° C. during the predrying; and
   d. subsequently burning in oxygen, within the closed pressure vessel, the predried biomaterial in the presence of the water vapor generated during pre-drying and which has been condensed on the wall of the pressure vessel.

2. The processing method according to claim 1 wherein said pre-drying is performed at a pressure of 20 mbar and a temperature of 110° C.

3. The processing method of claim 1 comprising pre-drying 20 g of a sample of the biomaterial with a water content of 80% in a closed pressure vessel at a pressure of about 20 mbar down to a residual moisture of 5 to 10% and subsequently burning the pre-dried sample in oxygen at 30 to 40 bar.

4. A processing method for breaking down biomaterials comprising: disposing approximately 5 grams of the water-free biomaterial in a sample container within a pressure vessel; adding approximately 1 ml of distilled water to the sample container; placing approximately 10 ml of distilled water in the bottom part of the pressure vessel and closing the vessel; cooling the wall of the pressure vessel to approximately 10° C; predrying said sample by evaporating the water in the sample container; subsequently burning said predried biomaterial in oxygen under pressure in the presence of water vapor condensed on the wall of said pressure vessel.

5. A processing method for breaking down biomaterials comprising:
   a. comminuting the sample of biomaterial;

b. placing the comminuted sample in a closed pressure vessel;
c. evacuating said vessel to a pressure of approximately 20 mbar;
d. heating the biomaterial to a temperature of about 110° C; and
e. subsequently burning said pre-dried biomaterial in oxygen at a pressure of about 30 to 40 bar.

6. The method of claim 5 wherein said sample of biomaterial is a moist sample and wherein said heating step is carried out to pre-dry said sample down to a residual moisture of 5–10%.

7. The method according to claim 6 wherein 20–30 g. of a sample of the biomaterial with a water content of 70–90% are used.

8. The method according to claim 6 wherein said sample is a 20 g. sample of biomaterial with a water content of approximately 80%.

9. The method according to claim 5 wherein said sample of biomaterial is water free and further including the step of placing a quantity of distilled water in said pressure vessel.

10. The method according to claim 9 wherein 5 g. of water free biomaterial are used to which 1 ml. of distilled water is added with an additional 9 ml. of distilled water placed in the bottom part of said closed pressure vessel.

11. The method according to claim 9 wherein said pressure vessel has a volume of about 1.5 l and further including adding about 10 ml. of distilled water to said dry material.

12. A method according to claim 5 and further including the step of cooling the wall of said pressure vessel to about 10° C. in order to condense water vapor generated during said heating step.

* * * * *